(12) United States Patent
Kitagawa et al.

(10) Patent No.: US 9,009,902 B2
(45) Date of Patent: Apr. 21, 2015

(54) ELECTRIC TOOTHBRUSH

(75) Inventors: Tadanobu Kitagawa, Shiga-ken (JP); Yoshihiro Kitamura, Shiga-ken (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 365 days.

(21) Appl. No.: 13/512,499

(22) PCT Filed: Dec. 15, 2010

(86) PCT No.: PCT/JP2010/072516
§ 371 (c)(1),
(2), (4) Date: May 29, 2012

(87) PCT Pub. No.: WO2011/078020
PCT Pub. Date: Jun. 30, 2011

(65) Prior Publication Data
US 2012/0233788 A1    Sep. 20, 2012

(30) Foreign Application Priority Data
Dec. 25, 2009   (JP) .................. 2009-294636

(51) Int. Cl.
*A61C 17/16* (2006.01)
*A61C 17/34* (2006.01)
*A61C 17/22* (2006.01)

(52) U.S. Cl.
CPC ........... *A61C 17/3481* (2013.01); *A61C 17/222* (2013.01); *A61C 17/225* (2013.01)

(58) Field of Classification Search
CPC . A61C 17/3481; A61C 17/222; A61C 17/225
USPC .................................... 15/22.1, 22.2, 167.1
See application file for complete search history.

(56) References Cited

U.S. PATENT DOCUMENTS

| | | |
|---|---|---|
| 5,974,615 A | 11/1999 | Schwarz-Hartmann et al. |
| 7,240,390 B2 | 7/2007 | Pfenniger et al. |
| 7,713,461 B2 | 5/2010 | Pfenniger et al. |
| 8,307,488 B2 | 11/2012 | Pfenniger et al. |
| 2002/0120991 A1* | 9/2002 | Cacka et al. ................... 15/22.1 |
| 2004/0060138 A1 | 4/2004 | Pfenniger et al. |

(Continued)

FOREIGN PATENT DOCUMENTS

| | | |
|---|---|---|
| CN | 1034124 A | 7/1989 |
| CN | 1692007 A | 11/2005 |

(Continued)

OTHER PUBLICATIONS

Search Report for corresponding European Patent Application No. 10839253.1, dated May 21, 2013, pp. 1-8.

(Continued)

*Primary Examiner* — Shay Karls
(74) *Attorney, Agent, or Firm* — Wolf, Greenfield & Sacks, P.C.

(57) ABSTRACT

On a tip of a main body case is formed a cylindrical brush attachment shaft tube to which a toothbrush head (holding unit) is removably attached. In a space within the cylindrical brush attachment shaft tube is disposed a motor to which an eccentric weight generating vibration is attached. Therefore, it is possible for the tip of the toothbrush head to approach the main body case side by the length of the cylindrical brush attachment shaft tube, thereby shortening the total length of an electric toothbrush.

5 Claims, 5 Drawing Sheets

(56) References Cited

U.S. PATENT DOCUMENTS

| | | |
|---|---|---|
| 2007/0163061 A1 | 7/2007 | Sorrentino |
| 2007/0222109 A1 | 9/2007 | Pfenniger et al. |
| 2011/0024944 A1 | 2/2011 | Pfenniger et al. |

FOREIGN PATENT DOCUMENTS

| | | |
|---|---|---|
| EP | 2008-212200 A | 9/2008 |
| JP | 64-4222 U | 1/1989 |
| JP | 2-2028 U | 1/1990 |
| JP | 6-42661 Y2 | 1/1990 |
| JP | 08-000358 | 6/1994 |
| JP | 8-010705 A | 1/1996 |
| JP | 9-168554 A | 6/1997 |
| JP | 2003-245288 A | 9/2003 |
| JP | 2004-057534 A | 2/2004 |
| JP | 3134115 U | 8/2007 |
| RU | 2181991 C2 | 5/2002 |
| WO | WO 98/01083 | 1/1998 |

OTHER PUBLICATIONS

Office Action from corresponding Korean Patent Application No. 10-2012-7013670, dated Sep. 5, 2013, pp. 1-5.

International Preliminary Report on Patentability in PCT/JP2010/072516 (parent application) dated Aug. 14, 2012.

Office Action from corresponding Russian Patent Application No. 2012121825, dated Feb. 27, 2013, pp. 1-3.

Office Action from corresponding Chinese Application No. 201080054796.9 dated Jul. 7, 2014, including English summary.

* cited by examiner

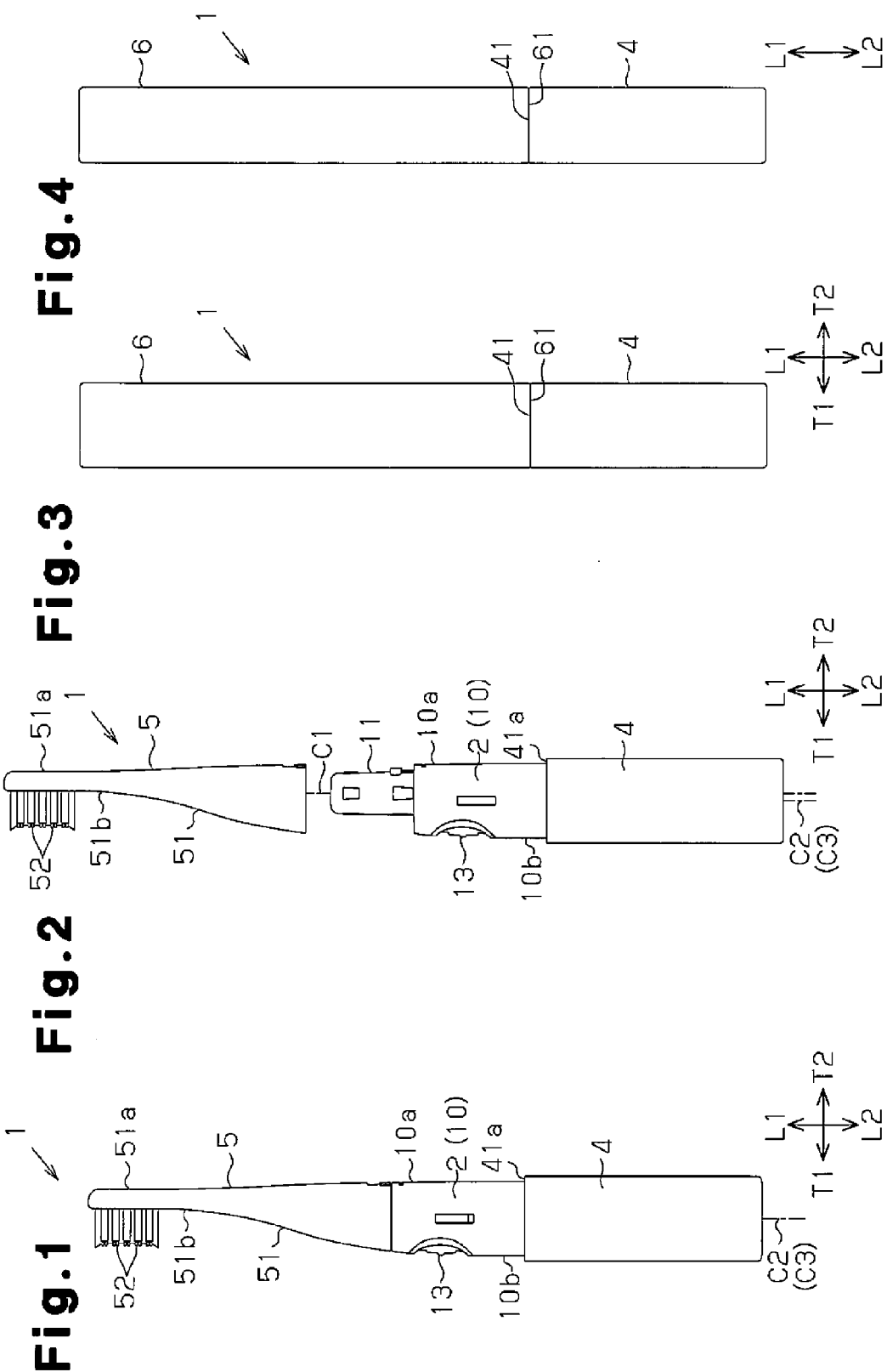

ELECTRIC TOOTHBRUSH

TECHNICAL FIELD

The present invention relates to an electric toothbrush.

BACKGROUND ART

In the prior art, various types of electric toothbrushes (e.g., patent document 1) have been proposed in which the toothbrush rotates an eccentric weight with a motor to generate oscillation and transmit the oscillation to the toothbrush bristles so as to improve the plaque removal performance (teeth brushing performance).

Over these recent years, people have become conscious of oral hygiene and thus have started to brush their teeth when at work or while traveling. As a result, electric toothbrushes having superior brushing functions are more frequently used when people brush their teeth at work, while traveling, or the like.

PRIOR ART LITERATURE

Patent Document

Patent Document 1: Japanese Laid-Open Patent Publication No. 9-168554

SUMMARY OF THE INVENTION

Problems that are to be Solved by the Invention

An electric toothbrush requires an oscillation generator, which is formed by a motor including an eccentric weight, a battery, which drives the oscillation generator, and the like. This enlarges the toothbrush making the toothbrush bulky and inconvenient when carried in a bag, a pouch, or a pocket.

Thus, there is a demand for a toothbrush that is compact and has superior portability but does not lower the teeth brushing performance.

The present invention solves the above problem. The object of the present invention is to provide an electric toothbrush that is compact and has superior portability and superior teeth brushing performance.

Means for Solving the Problem

The means for achieving the above object will now be described.

An electric toothbrush of the present invention is provided with a toothbrush head, an oscillation generator formed by a motor including an eccentric weight, and a main body case attached in a removable manner to the toothbrush head and accommodating the oscillation generator. The toothbrush head is attached to a brush attachment shaft tube at a distal end of the main body case, and the oscillation generator is arranged in the brush attachment shaft tube.

In the electric toothbrush, preferably, the brush attachment shaft tube is arranged biased toward a rear surface side of the main body case.

The electric toothbrush, preferably, further includes a cap fitted onto the main body case to accommodate the toothbrush head that is attached to the brush attachment shaft tube.

In the electric toothbrush, preferably, the main body case includes an outer case, which includes the brush attachment shaft tube, and an inner case, which includes a motor accommodation portion that accommodates the motor at one end and a battery accommodation portion that accommodates a battery for driving the motor at another end. The inner case is accommodated in the outer case so that the motor accommodation portion is press-fitted into the brush attachment shaft tube of the outer case.

The electric toothbrush, preferably, further includes a seal ring arranged between the outer case and the inner case of the main body case.

In the electric toothbrush, preferably, the brush attachment shaft tube is entirely arranged in the toothbrush head when the toothbrush head is attached to the main body case.

Effect of the Invention

The present invention provides an electric toothbrush that is compact and has superior portability and superior teeth brushing performance.

BRIEF DESCRIPTION OF THE DRAWINGS

FIG. 1 is a side view of an electric toothbrush in a first embodiment;

FIG. 2 is a side view showing the electric toothbrush from which a toothbrush head is removed;

FIG. 3 is a side view showing the electric toothbrush to which a cap is attached;

FIG. 4 is a front view showing the electric toothbrush to which the cap is attached;

EMBODIMENTS OF THE INVENTION

Figure 5:
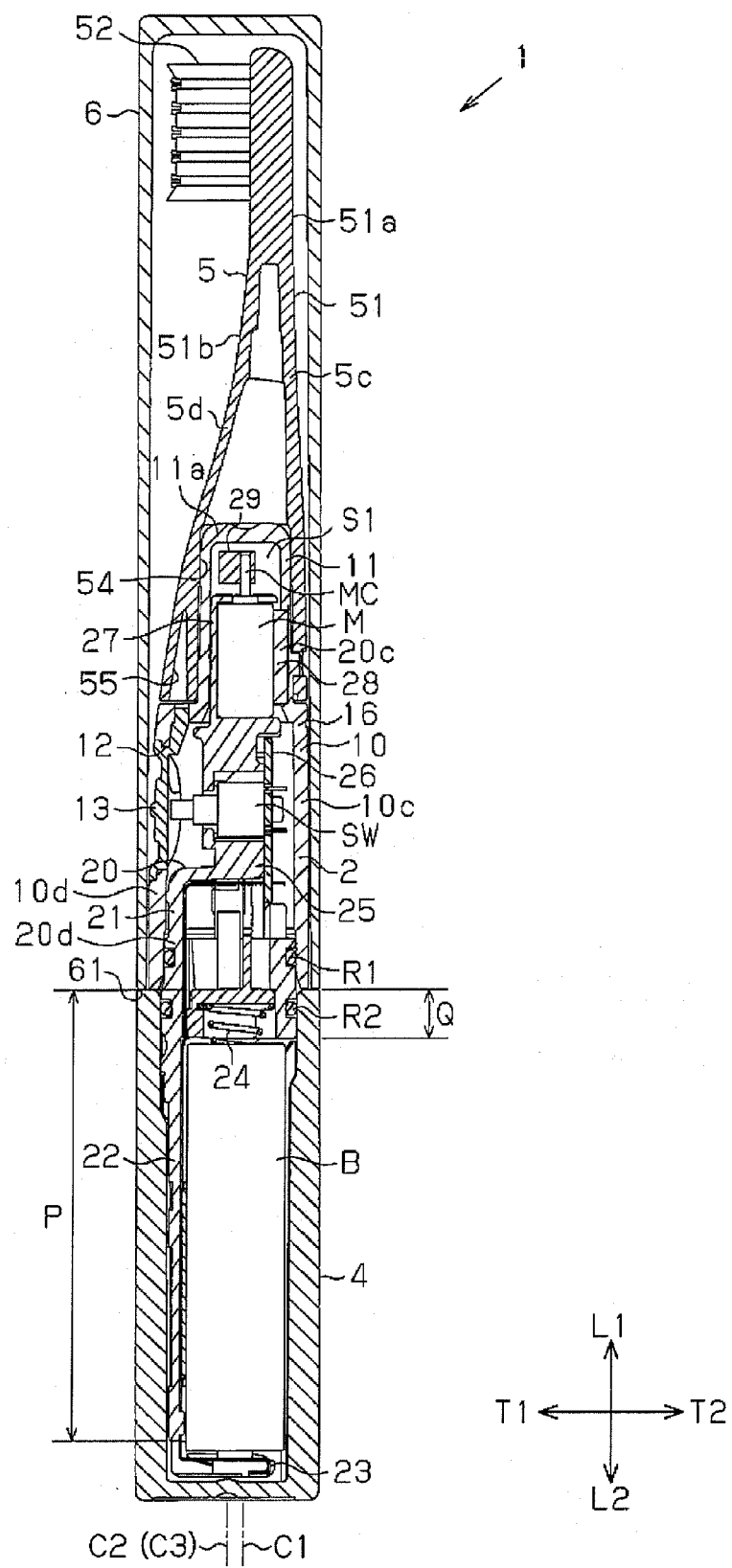
FIG. 5 is a cross-sectional side view showing the electric toothbrush.

A first embodiment of the present invention will now be described with reference to the drawings.

In the drawings, arrows L1, L2, T1, and T2 respectively indicate a distal direction L1, a basal direction L2, a frontward direction T1, and a rearward direction T2.

Referring to FIG. 1, an electric toothbrush 1 includes a main body case 2, a grip case 4, which is fitted to a basal side of the main body case 2, a toothbrush head 5, which is fitted to a distal side of the main body case 2, and a cap 6, which is fitted to the main body case 2 attached with the toothbrush head 5 as shown in FIG. 3.

Figure 6:
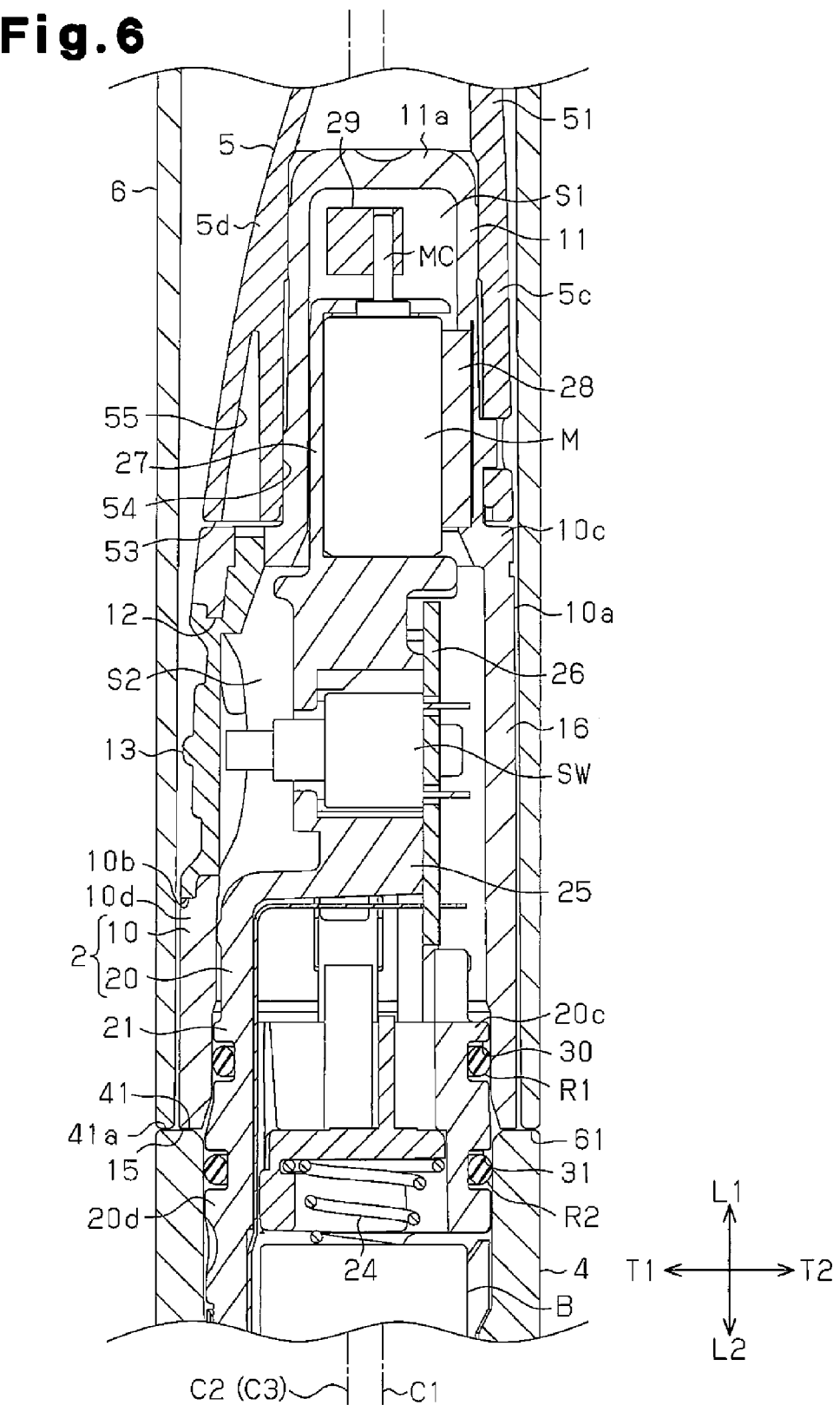
FIG. 6 is an enlarged cross-sectional side view showing part of the electric toothbrush.

Referring to FIGS. 5 and 6, the main body case 2 includes an outer case 10 and an inner case 20. The outer case 10 accommodates the inner case 20, and the inner case 20 accommodates electric components that apply oscillation to the toothbrush head 5.

With reference to FIGS. 5 and 6, the terms related to the electric toothbrush 1 will now be defined:

(A) A cross-sectional plane that includes a rotation shaft MC of a motor M and brush bristles 52 of the toothbrush head 5 and is parallel to the rotation shaft MC of the motor M defines a cross-sectional side plane;

(B) In the cross-sectional side plane, the side of a center axis C3 of the grip case 4 including a distal end portion of the brush bristles 52 of the toothbrush head 5 is defined as a front side. In the cross-sectional side plane, the side of the center axis C3 of the grip case 4 opposite to the front side defines a rear side;

(C) In a direction extending along the center axis C3 of the grip case 4, a portion of the outer case 10 located between the toothbrush head 5 and the grip case 4 is defined as a case intermediate portion 16. Further, in the cross-sectional side plane, walls at the front side of the outer case 10, the inner case 20, and the toothbrush head 5 are respectively defined as front walls 10d, 20d, and 5d. In the cross-sectional side plane, walls at the rear side of the outer case 10, the inner case 20, and the toothbrush head 5 are respectively defined as rear walls 10c, 20c, and 5c;

(D) In the cross-sectional side plane, an outer surface of the front wall 5d in the toothbrush head 5 is defined as a front surface 51b. Further, an outer surface of the rear wall 5c in the toothbrush head 5 is defined as a rear surface 51a; and (E) Among the end portions of the toothbrush head 5, the side of the brush bristles 52 is defined as a distal end portion. Further, among the end portions of the toothbrush head 5, the end portion opposite to the distal end portion is defined as a basal end portion.

As shown in FIGS. 5 and 6, the outer case 10 is a case having the form of a bottomed tetragonal tube that is chamfered and formed from ABS resin. Part of the distal side of the outer case 10 is narrowed to form a brush attachment shaft tube 11. The brush attachment shaft tube 11, which has the form of a bottomed tetragonal tube, includes a distal end portion closed by a top wall 11a. The brush attachment shaft tube 11 is hollow and defines, for example, a tubular void S1 (refer to FIG. 6). The void S1 is in communication with a void S2 (refer to FIG. 6), which has the form of a tetragonal tube, in the outer case 10. As shown in FIG. 2, the center axis C1 of the brush attachment shaft tube 11 is biased toward the rear surface 10a of the outer case from the center axis C2 of the outer case 10.

The brush attachment shaft tube 11 is fitted into the toothbrush head 5 from an open basal end of the toothbrush head 5. In the case intermediate portion 16, the end portion at the side of the toothbrush head 5 is arranged continuously with the brush attachment shaft tube 11. The front wall 10d of the case intermediate portion 16 is arranged in front of the front wall 10d of the brush attachment shaft tube 11. This forms a step at the boundary between the case intermediate portion 16 and the brush attachment shaft tube 11. The toothbrush head 5 is attached to the main body case 2 so that an end face 53 of the basal end portion of the toothbrush head 5 faces toward an end face of the step.

In the cross-sectional side plane, the front wall 20d of the inner case 20 is arranged at the front side of the motor M. The front wall 10d of the outer case 10 is arranged at the front side of the front wall 20d of the inner case 20. The front wall 5d of the toothbrush head 5 is arranged at the front side of the front wall 10d.

A through hole 12 extends through the front surface 10b of the outer case 10. The through hole 12 is closed by an elastic switch member 13. The switch member 13 is formed by an elastomer resin and welded to the rim of the through hole 12. A user can push the switch member 13 into the void S2.

The voids S1 and S2 of the outer case 10 accommodate the inner case 20. The inner case 20 includes a trunk 21, which has the form of a chamfered tetragonal tube at a generally central position. The trunk 21 has a profile having the same shape as the inner circumferential surface of the outer case 10. About one half of the trunk 21 at the distal side is arranged in the void S2 of the outer case 10.

The trunk 21 includes a basal end portion defining a battery accommodation portion 22 formed by cutting out one half of a bottomed tubular body and opening the rear side. When about one half of the trunk 21 at the distal side is arranged in the void S2 of the outer case 10, the battery accommodation portion 22 is not accommodated in the outer case 10 and is exposed in the basal direction L2 from the outer case 10. A positive electrode terminal fitting 23 and a negative electrode terminal spring 24, which extends from the trunk 21, are arranged in the battery accommodation portion 22. A battery B, for example an AAA battery, is accommodated and held in the battery accommodation portion 22 in a state electrically connected to the positive electrode terminal fitting 23 and the negative electrode terminal spring 24.

The distal side of the trunk 21 defines a substrate fastening portion 25. The substrate fastening portion 25 is arranged at a location where it faces the switch member 13, which is arranged in the outer case 10, when about half of the trunk 21 at the distal side is arranged in the void S2 of the outer case 10. A printed wiring substrate 26 is fixed to the substrate fastening portion 25. A switch SW, which is electrically connected to the positive electrode terminal fitting 23 and the negative electrode terminal spring 24, is mounted on the printed wiring substrate 26. The printed wiring substrate 26 is positioned to face the switch member 13, which is arranged in the outer case 10. Accordingly, when the switch member 13 is pushed with a finger, the switch SW is turned on and off by the pushed switch member 13.

The distal side of the substrate fastening portion 25 includes a motor accommodation portion 27, which is formed by cutting out one half of a bottomed tubular body and opening the rear side. When the trunk 21 is arranged in the void S2 of the outer case 10 of the trunk 21, the motor accommodation portion 27 is arranged in the void S1 of the brush attachment shaft tube 11. When the motor accommodation portion 27 is arranged in the void S1 of the brush attachment shaft tube 11, the outer circumferential surface of the motor accommodation portion 27 comes into close contact with the inner circumferential surface of the brush attachment shaft tube 11.

As shown in FIGS. 5 and 6, the motor accommodation portion 27 accommodates a motor M. When the motor accommodation portion 27 is arranged in the void S1 of the brush attachment shaft tube 11, the outer circumferential surface of the motor M, which is exposed from the motor accommodation portion 27, comes into contact with the inner circumferential surface of the brush attachment shaft tube 11 through a spacer 28, which serves as a transmission member. The rotation shaft MC of the motor M is arranged toward the rear from the center axis C2 of the grip case 4. Further, the rotation shaft MC projects into the void S1 from the distal surface of the motor accommodation portion 27. An eccentric weight 29 is fixed to a projecting portion of the rotation shaft MC.

The front outer surface of the motor M directly contacts the front wall 20d of the inner case 20.

As shown in FIGS. 5 and 6, the spacer 28 is arranged between the rear outer surface of the motor M and the rear wall 20c of the inner case 20. The spacer 28 directly contacts both of the rear wall 10c of the outer case 10 and the motor M.

In the cross-sectional side plane, the front wall 20d of the inner case 20 is arranged at the front side of the motor M. The front wall 10d of the outer case 10 is arranged at the front side of the front wall 20d of the inner case 20. The front wall 5d of the toothbrush head 5 is arranged at the front side of the front wall 10d of the outer case 10. The spacer 28 is arranged at the rear side of the motor M. The rear wall 10c of the outer case 10 is arranged at the rear side of the spacer 28. The rear wall 5c of the toothbrush head 5 is arranged at the rear side of the outer case 10.

The switch SW is arranged on the front wall 20d of the inner case 20. In the inner case 20, the switch SW is arranged, relative to the center axis C3 of the grip case 4, at a portion located on the opposite side of the portion where the spacer 28 is arranged.

When the switch SW mounted on the printed wiring substrate 26 is turned on, the motor M receives voltage from the battery B and produces rotation. When the motor M produces rotation, the eccentric weight 29, which is fixed to the rotation shaft MC, rotates eccentrically about the rotation shaft MC. The eccentric rotation swings the rotation shaft MC and oscillates the motor M, which is accommodated and held in the motor accommodation portion 27. The oscillation of the motor M is transmitted through the motor accommodation portion 27 to the brush attachment shaft tube 11, which is in close contact with the motor accommodation portion 27.

One half of the outer circumferential surface of the trunk 21 of the inner case 20 at the distal side, which is arranged in the outer case 10, has a smaller diameter than the other half at the basal side, which is not arranged in the outer case 10. Thus, when the motor accommodation portion 27 of the inner case 20 is arranged in the void S1 in the distal half of the outer case 10 and the substrate fastening portion 25 of the inner case 20 is arranged in the void S2, the outer circumferential surface of the basal half of the trunk 21 engages the inner circumferential surface of the outer case 10. This restricts further movement of the inner case 20. Thus, the inner case 20 is arranged so that the distal half of the trunk 21 is arranged in the outer case 10, and the basal half of the trunk 21 and the battery accommodation portion 22 is exposed from the outer case 10.

A distal annular groove 30 is formed in the outer circumferential surface of the distal half of the trunk 21. A seal ring R1, which serves as a second elastic member, is fitted in the distal annular groove 30. The seal ring R1, which is formed by a rubber O-ring, includes an outer portion that projects from the outer circumferential surface of the trunk 21 in a state fitted to the distal annular groove 30. Accordingly, when the inner case 20 (trunk 21) is arranged in the outer case 10, the seal ring R1 of the distal annular groove 30 is elastically deformed by the inner circumferential surface of the outer case 10 so that the space between the inner case 20 (trunk 21) and the outer case 10 is watertight and elastically supported.

As shown in FIGS. 5 and 6, an open end face 15, which serves as an end face of the basal end portion of the outer case 10, and an open end face 41 of the distal end portion of the grip case 4, face each other. A basal annular groove 31 is formed in the circumferential surface of the basal half of the trunk 21, and an elastic ring R2, which serves as an elastic member, is fitted in the basal annular groove 31. The elastic ring R2 is a ring made of an elastic synthetic resin. The present embodiment employs a rubber O-ring used as a seal member. The elastic ring R2 includes an outer portion that projects from the outer circumferential surface of the trunk 21 in a state fitted to the basal annular groove 31.

The main body case 2, which is formed in this manner, is attached to the grip case 4 at the basal side and attached to the toothbrush head 5 at the distal side.

The grip case 4 is a case having the form of a chamfered bottomed tetragonal tube that is formed from ABS resin. The battery accommodation portion 22 of the inner case 20 in the main body case 2 is arranged inside the grip case 4 from a distal opening. The shape of the inner circumferential surface of the distal opening of the grip case 4 conforms to the shape of the outer circumferential surface of the basal half of the trunk 21 so that the basal half of the trunk 21 can be arranged in the grip case.

Here, the outer case 10 is not arranged in the grip case 4, and the open end face 15 of the outer case 10 contacts the open end face 41 of the grip case 4. The grip case 4 has a larger outer diameter than the outer case 10. Accordingly, when joining the open end face 15 of the outer case 10 and the open end face 41 of the grip case 4, the outer circumferential surface of the grip case 4 projects outward from the outer circumferential surface of the outer case 10. The open end face 41 of the grip case 4 exposed to the outer side defines a step surface 41a.

As shown in FIGS. 5 and 6, the elastic ring R2 is arranged between the inner circumferential surface of the distal end portion of the grip case 4 and the outer surface of the inner case 20. When the inner case 20 (trunk 21) is arranged in the grip case 4, the elastic ring R2 of the basal annular groove 31 is elastically deformed at the inner surface of the distal opening of the grip case 4 so that the space between the inner case 20 (trunk 21) and the grip case 4 is watertight and elastically supported. The attachment of the main body case 2 to the grip case 4 forms a grip of the electric toothbrush 1 with the grip case 4 and hermetically accommodates the battery B, which is accommodated and held in the battery accommodation portion 22, with the grip case 4.

When a length of a portion in the front wall 20d of the inner case 20 that directly faces the grip case 4 is represented by length P and a length of a portion in the rear wall of the inner case 20 that directly faces the grip case 4 is represented by length Q, length Q is less than length P.

The toothbrush head 5, which is attached to the distal side of the main body case 2, includes a holding part 51. The brush bristles 52 are embedded in the distal end portion of the holding part 51. The basal end of the holding part 51 has a profile having the same shape as the profile of the outer case 10. The basal end face 53 of the holding part 51 includes a fitting hole 54. The brush attachment shaft tube 11, which is formed on the outer case 10, is press-fitted in a removable manner to the fitting hole 54. When the brush attachment shaft tube 11 is press-fitted, the inner circumferential surface of the fitting hole 54 comes into close contact with the outer circumferential surface of the brush attachment shaft tube 11. Accordingly, the oscillation of the motor M, which is transmitted to the brush attachment shaft tube 11 through the motor accommodation portion 27, is transmitted to the brush bristles 52 at the distal end portion through the holding part 51 of the toothbrush head 5.

The holding part 51 is formed to narrow from the basal end toward the distal end portion. More specifically, the holding part 51 is formed so that the front surface 51b approaches the rear surface 51a, and the left and right surfaces approach each other. That is, the distal end portion of the holding part 51 is arranged so that the distal rear surface 51a is located rearward from the center axis C1 of the brush attachment shaft tube 11 and frontward from the rear surface 10a of the outer case 10 and so that the tips of the embedded brush bristles 52 do not extend outward from the front surface 10b of the outer case 10. Further, the front surface 51b of the holding part 51 is arranged rearward closer to the rear surface 51a so that the distal end portion of the holding part 51 is arranged at a rearward position. Since the front surface of the holding part 51 does not extend outward, when brushing teeth, the teeth do not hit such an outwardly extending portion that would make brushing difficult.

In the cross-sectional plane, the front walls 10d and 20d have thickness X1, the front wall 5d of the toothbrush head 5 has thickness Y1, the rear walls 10c and 20c of the main body case 2 have thickness X2, and the rear wall 5c of the toothbrush head 5 has thickness Y2.

Figure 7:
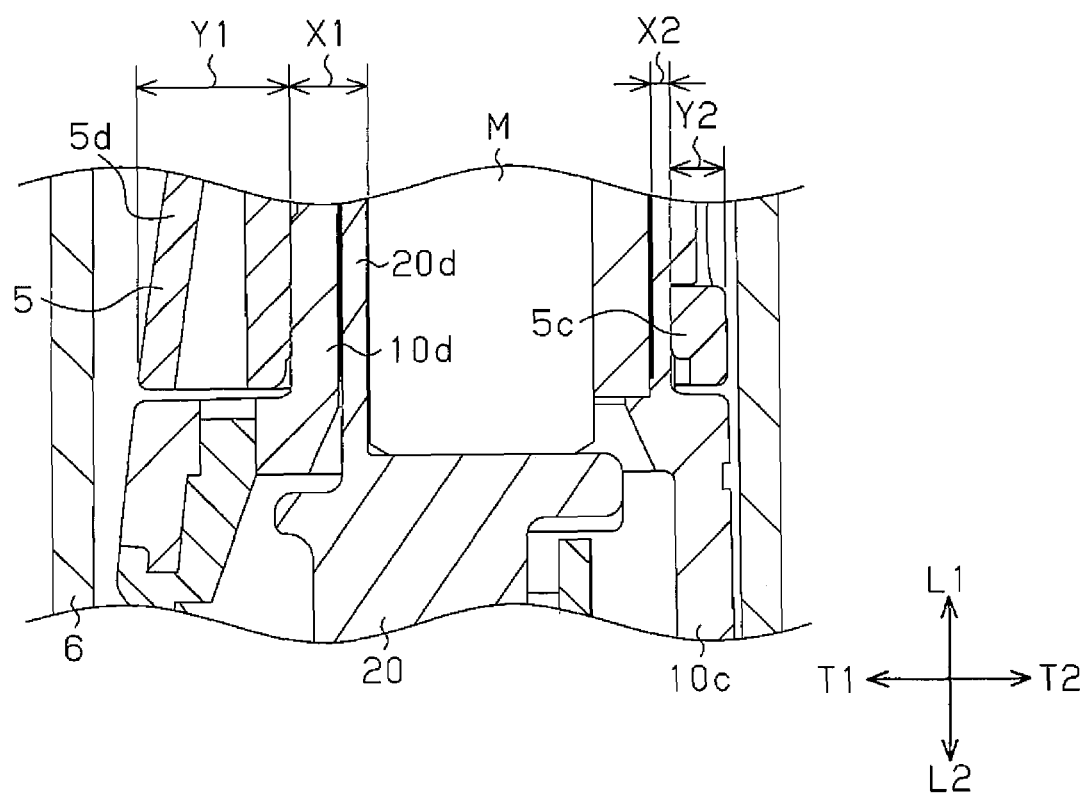
FIG. 7 is an enlarged cross-sectional side view showing part of the electric toothbrush.

As shown in FIG. 7, in the end face 53 of the basal end of the toothbrush head 5 and a plane parallel to and including the end face 53, a thickness obtained by adding the thickness X1 and the thickness Y1 is greater than a thickness obtained by adding the thickness X2 and the thickness Y2.

In the toothbrush head 5, when a length of the front surface 51b from the basal end portion to the distal end portion is represented by length V, and a length of the rear surface 51a from the basal end portion to the distal end portion is represented by length W, the length W of the rear surface 51a is less than the length V of the front surface 51b. Further, the front wall 5d of the toothbrush head 5 includes a hollow portion 55 at a location corresponding to the motor M.

The motor M, which is an oscillation source, is accommodated in the brush attachment shaft tube 11, and the brush attachment shaft tube 11 is press-fitted to the holding part 51 of the toothbrush head 5. Thus, the distal end of the holding part 51 can be arranged closer to (near) the main body case 2 for a length corresponding to the brush attachment shaft tube 11 (overlapped amount of the brush attachment shaft tube 11 and the holding part 51). As a result, the entire length of the electric toothbrush 1 can be shortened so that the electric toothbrush 1 has superior portability and can easily be held in a pouch or a pocket. It is preferable that the entire brush attachment shaft tube 11 be arranged in the toothbrush head 5 like in the illustrated example.

As shown in FIGS. 5 and 6, the toothbrush head 5 attached to the main body case 2 is accommodated in the cap 6. The cap 6, which is a case having the form of a chamfered bottomed tetragonal tube that is formed from ABS resin, can be attached in a removable manner to the main body case 2. When the cap 6 is attached to the main body case 2, the outer circumference of the basal end portion of the toothbrush head 5 is covered by the cap 6.

The toothbrush head 5 and the main body case 2 are fitted into the basal opening of the cap 6 and arranged in the cap 6. The inner circumferential surface in the basal opening of the cap 6 has the same shape as the outer circumferential surface of the main body case 2. When the cap 6 is attached to the main body case 2, the basal side of the cap 6 comes into contact with the open end face 41 (step surface 41a) of the grip case 4. This restricts further movement of the main body case 2.

The cap 6 has a profile having the same shape as the profile of the grip case 4. When the cap 6 is attached to the main body case 2, as shown in FIGS. 3 and 4, the outer circumferential surface of the cap 6 is flush with the outer circumferential surface of the grip case 4, and the boundary of the cap 6 and the grip case 4 is unnoticeable. That is, the outer circumferential surface of the cap 6 at the side of a basal end face 61 and the outer circumferential surface at the side of the open end face 41 form a continuous surface in a state in which the cap 6 is fitted to the main body case 2. As a result, the outer circumferential surface of the electric toothbrush 1 is smooth. Thus, when the electric toothbrush 1 is accommodated in a pouch or a pocket, the electric toothbrush 1 does not get hooked to the surrounding, and the cap 6 does not fall off.

Further, when the cap 6 is attached to the main body case 2, the switch member 13 arranged on the main body case 2 is arranged in the cap 6. Thus, when the electric toothbrush 1 is accommodated in a pouch or a pocket, the switch member 13 is not erroneously turned on.

The advantages of the electric toothbrush 1 will now be described.

(1) In the present embodiment, the tubular brush attachment shaft tube 11, which is attached in a removable manner to the toothbrush head 5 (holding part 51), is arranged on the distal end of the main body case 2, and the motor M, which is attached to the eccentric weight 29 and generates oscillation, is arranged in the brush attachment shaft tube 11. Accordingly, the distal end of the toothbrush head 5 can be arranged closer to the main body case 2 by an amount corresponding to the length of the brush attachment shaft tube 11. As a result, the electric toothbrush 1 can be shortened in length and has superior portability in which it can easily be put into a pouch or a pocket.

(2) In the present embodiment, the toothbrush head 5 (holding part 51) is attached to the brush attachment shaft tube 11, which is arranged in the motor M to which the eccentric weight 29 that generates oscillation is attached. Accordingly, the brush bristles 52 embedded in the distal end portion of the toothbrush head 5 can be arranged closer to the motor M. This suppresses attenuation of the oscillation of the motor M, and the oscillation is efficiently transmitted to the brush bristles 52. This improves the teeth brushing performance.

(3) In the present embodiment, the motor M, which generates oscillation and is arranged in the brush attachment shaft tube 11, is located at a position that is far from the grip case 4, which is held and fixed by a hand. This allows the movement of the distal end portion of the toothbrush head 5 to be enlarged and further improves the teeth brushing performance.

(4) In the present embodiment, the brush attachment shaft tube 11 is biased toward the rear surface 10a of the main body case 2, and the front surface of the basal end portion of the holding part 51 holding the brush bristles 52 is arranged rearward toward the rear surface 51a. Further, the holding part 51 of the toothbrush head 5 is narrowed from the basal end toward the distal end portion. In addition, the front surface of the holding part 51 is formed closer to the rear surface 51a. As a result, since the front surface of the holding part 51 does not extend outward, when brushing teeth, the teeth do not hit such an outwardly extending portion that would make brushing difficult.

(5) In the present embodiment, the main body case 2 is formed by the outer case 10, which includes the brush attachment shaft tube 11, and the inner case 20, which includes the motor accommodation portion 27 that accommodates the motor M at one end and the battery accommodation portion 22 that accommodates the battery B at the other end. Accordingly, just by accommodating the inner case 20 in the outer case 10, the motor accommodation portion 27 can be press-fitted into the brush attachment shaft tube 11 of the outer case 10, and the coupling of the motor M to the brush attachment shaft tube 11 is facilitated.

(6) In the present embodiment, the elastic ring R2 is arranged between the main body case 2, or the trunk 21 of the inner case 20, and the grip case 4. When the inner case 20 (trunk 21) is arranged in the grip case 4, the elastic ring R2 is elastically deformed by the inner surface of the distal opening of the grip case 4 so that the space between the inner case 20 and the grip case 4 is watertight and elastically supported.

Accordingly, the elastic ring R2 suppresses the transmission of the oscillation of the motor M, which is accommodated in the motor accommodation portion 27 of the inner case 20, to the grip case 4, and the oscillation is transmitted in a concentrated manner at the side of the toothbrush head 5. As a result, the brushing performance is further improved, the oscillation transmitted to the hand holding the grip case 4 is decreased, and the teeth are brushed with comfort.

Moreover, the elastic ring R2 has a sealing performance. Thus, when washed with water, water can be prevented from entering the main body case 2 through between the grip case 4 and the inner case 20.

(7) In the present embodiment, the seal ring R1 is arranged between the outer case 10 of the main body case 2 and the trunk 21 of the inner case 20. When washing the electric toothbrush 1 with water, water can be prevented from entering the main body case 2 through between the outer case 10 and the inner case 20.

Moreover, the transmission of oscillation of the motor M, which is accommodated in the motor accommodation portion 27 of the inner case 20, by the seal ring R1 to the outer case 10 is suppressed and transmitted in a concentrated manner at the side of the toothbrush head 5. As a result, the teeth brushing performance can be further improved, the oscillation transmitted to the hand holding the outer case 10 is decreased, and the teeth are brushed with comfort.

(8) In the present embodiment, the toothbrush head 5 attached to the main body case 2 is accommodated in the cap 6 when not in use. When carrying the electric toothbrush 1, the toothbrush head 5 (brush bristles 52) does not touch the surrounding. This maintains a hygiene state without the toothbrush head 5 becoming unclean or a pouch, pocket, or the like from becoming unclean. Further, the brush bristles 52 can be protected without being deformed, and a high rubbing performance can be maintained. Further, the switch member 13 is not erroneously operated by the surrounding.

Moreover, when attached to the main body case 2, the profile of the cap 6 is such that the outer circumferential surface of the electric toothbrush 1 is flush with the outer circumferential surface of the grip case 4. As a result, the outer circumferential surface of the electric toothbrush 1 is smooth. Thus, when accommodated in a pouch or a pocket, the electric toothbrush 1 does not get hooked to the surrounding, and the cap 6 does not fall off.

The above embodiment may be modified as described below.

In the above embodiment, the main body case 2 is formed by two members, the outer case 10 and the inner case 20. However, the outer case 10 and the inner case 20 may be formed integrally to obtain the main body case 2. This reduces the number of components and allows for the seal ring R1 to be omitted.

In the above embodiment, the elastic ring R2 is arranged between the trunk 21 of the inner case 20 and the grip case 4. Instead of a ring, elastic members may be arranged at predetermined intervals in the circumferential direction.

In the above embodiment, an O-ring that is elastic and has a sealing performance with respect to water is used as the elastic ring R2, which is arranged between the trunk 21 of the inner case 20 and the grip case 4. Instead, an elastic member that is just elastic and does not have a sealing performance with respect to water may be used.

Figure 8:
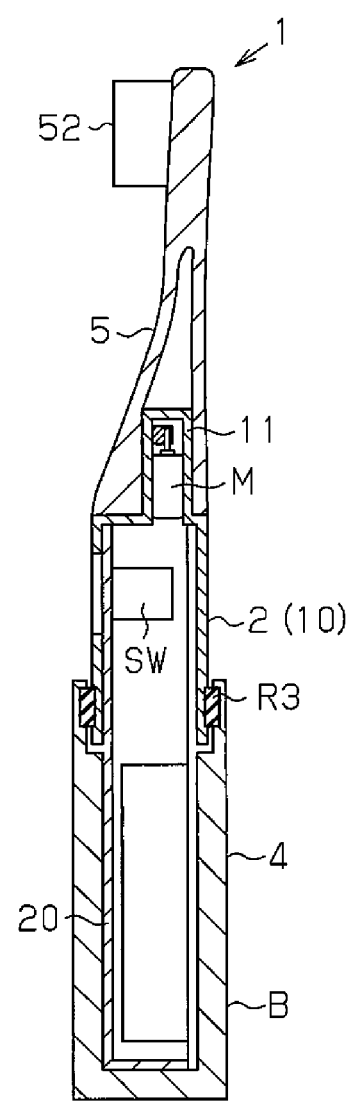
FIG. 8 is a cross-sectional side view showing an electric toothbrush in a further example.

In the above embodiment, the elastic ring R2 is arranged between the grip case 4 and the inner case 20 of the main body case 2. As shown in FIG. 8, the basal end portion in the outer case 10 of the main body case 2 may be inserted into the grip case 4, and an elastic ring R3 corresponding to the elastic ring R2 may be arranged between the grip case 4 and the outer case 10.

Description of the Reference Characters

1: electric brush, 2: main body case, 5: toothbrush head, 6: cap, 10: outer case, 10a: rear surface, 11: brush attachment shaft tube, 20: inner case, 22: battery accommodation portion, 27: motor accommodation portion, B: battery, M: motor, R1: seal ring.

The invention claimed is:
1. An electric toothbrush comprising:
a toothbrush head;
an oscillation generator formed by a motor including an eccentric weight; and
a main body case attached in a removable manner to the toothbrush head and accommodating the oscillation generator;
wherein
the toothbrush head is attached to a brush attachment shaft tube provided with a closed distal end portion at a distal end of the main body case,
the oscillation generator and the motor accommodation portion are arranged in the brush attachment shaft tube,
the main body case includes an outer case, which includes the brush attachment shaft tube, and an inner case, which includes a motor accommodation portion that accommodates the motor at one end a battery accommodation portion that accommodates a battery for driving the motor at another end, and
the inner case is accommodated in the outer case so that the motor accommodation portion is press-fitted into the brush attachment shaft tube of the outer case.

2. The electric toothbrush according to claim 1, wherein the brush attachment shaft tube is arranged biased toward a rear surface side of the main body case.

3. The electric toothbrush according to claim 1, further comprising a cap fitted onto the main body case to accommodate the toothbrush head that is attached to the brush attachment shaft tube.

4. The electric toothbrush according to claim 1, further comprising a seal ring arranged between the outer case and the inner case of the main body case.

5. The electric toothbrush according to claim 1, wherein the brush attachment shaft tube is entirely arranged in the toothbrush head when the toothbrush head is attached to the main body case.

* * * * *